United States Patent
Pacetti

(10) Patent No.: US 9,320,833 B2
(45) Date of Patent: Apr. 26, 2016

(54) POLYMERS OF FLUORINATED MONOMERS AND HYDROCARBON MONOMERS

(71) Applicant: Abbott Cardiovascular Systems Inc., Santa Clara, CA (US)

(72) Inventor: Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 430 days.

(21) Appl. No.: 13/967,262

(22) Filed: Aug. 14, 2013

(65) Prior Publication Data

US 2013/0330392 A1 Dec. 12, 2013

Related U.S. Application Data

(60) Continuation of application No. 12/558,341, filed on Sep. 11, 2009, now Pat. No. 8,529,931, which is a division of application No. 11/021,775, filed on Dec. 22, 2004, now Pat. No. 7,604,818.

(51) Int. Cl.

| | |
|---|---|
| *C08L 27/12* | (2006.01) |
| *C08L 23/04* | (2006.01) |
| *A61L 31/04* | (2006.01) |
| *A61L 31/10* | (2006.01) |
| *A61L 31/16* | (2006.01) |
| *C08F 214/18* | (2006.01) |
| *C08F 295/00* | (2006.01) |
| *C09D 127/16* | (2006.01) |
| *A61K 31/436* | (2006.01) |

(52) U.S. Cl.
CPC ............. *A61L 31/048* (2013.01); *A61K 31/436* (2013.01); *A61L 31/10* (2013.01); *A61L 31/16* (2013.01); *C08F 214/18* (2013.01); *C08F 295/00* (2013.01); *C09D 127/16* (2013.01); *A61L 2300/416* (2013.01)

(58) Field of Classification Search
USPC .................. 525/191; 424/423; 524/520, 544; 604/265

See application file for complete search history.

(56) References Cited

U.S. PATENT DOCUMENTS

| | | | | |
|---|---|---|---|---|
| 5,821,343 | A * | 10/1998 | Keogh | A61L 27/24 424/422 |
| 6,124,386 | A * | 9/2000 | Yokota | C08K 5/50 524/154 |
| 6,589,597 | B1 * | 7/2003 | Ono | C08F 210/02 264/460 |
| 6,926,919 | B1 * | 8/2005 | Hossainy | A61F 2/06 427/2.1 |
| 7,063,884 | B2 * | 6/2006 | Hossainy | A61F 2/06 428/212 |
| 7,192,638 | B2 * | 3/2007 | Tomihashi | C09D 127/18 428/327 |
| 7,604,818 | B2 * | 10/2009 | Pacetti | A61L 31/10 424/423 |
| 8,529,931 | B2 * | 9/2013 | Pacetti | A61L 31/10 424/423 |
| 2007/0003588 | A1 * | 1/2007 | Chinn | A61L 27/34 424/423 |
| 2007/0228617 | A1 * | 10/2007 | Higashi | C08F 214/26 264/446 |

* cited by examiner

*Primary Examiner* — Peter D Mulcahy
*Assistant Examiner* — Henry Hu
(74) *Attorney, Agent, or Firm* — Squire Patton Boggs (US) LLP

(57) ABSTRACT

It is provided an implantable device including a polymer blend that contains a polymer formed of fluorinated monomers and hydrocarbon monomers and another biocompatible polymer.

14 Claims, No Drawings

POLYMERS OF FLUORINATED MONOMERS AND HYDROCARBON MONOMERS

CROSS-REFERENCE TO RELATED APPLICATION

This application is a continuation application of U.S. application Ser. No. 12/558,341 filed on Sep. 11, 2009 now U.S. Pat. No. 8,529,931 which is a divisional application of U.S. application Ser. No. 11/021,775, filed on Dec. 22, 2004, now U.S. Pat. No. 7,604,818, the teachings of which are incorporated herein in their entirety by reference.

BACKGROUND OF THE INVENTION

1. Field of the Invention

This invention generally relates to a polymeric material useful for coating an implantable device, such as a stent.

2. Description of the Background

Although stents work well mechanically, the chronic issues of restenosis and, to a lesser extent, stent thrombosis remain. Pharmacological therapy in the form of a drug-delivery stent appears a feasible means to tackle these biologically derived issues. Polymeric coatings placed onto the stent serve to act both as the drug reservoir, and to control the release of the drug. One of the commercially available polymer coated products is a stent manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

The nature of the coating polymers plays an important role in defining the surface properties of a coating. For example, a very low $T_g$, amorphous coating material induces unacceptable rheological behavior upon mechanical perturbation such as crimping, balloon expansion, etc. On the other hand, a high $T_g$, or highly crystalline coating material introduces brittle fracture in the high strain areas of the stent pattern. Furthermore, a very low $T_g$, amorphous coating material can have a high drug permeability leading to an unacceptably high drug release rate. While a high $T_g$, or highly crystalline coating material can have a very low polymer permeability, which lead to an unacceptably low drug release rate. These are general principles which must also be combined with the properties of the drug such as the drug solubility in the polymer and in the tissue.

Some of the currently used polymeric materials have some undesirable properties such as lack of sufficient elongation to use on a stent or low permeability to drugs. One such polymer is poly(vinylidene fluoride) (PVDF). Therefore, there is a need for new polymeric materials suitable for use as coating materials on implantable devices.

The present invention addresses such problems by providing a polymeric material for coating implantable devices.

SUMMARY OF THE INVENTION

Provided herein is a polymer containing fluorinated monomers and hydrocarbon monomers useful for coating an implantable device such as a stent. The fluorinated monomers can provide mechanical strength for the polymer. The hydrocarbon monomers described herein impart flexibility to the polymer.

In one embodiment, the polymer can be a random or block polymer having a general formula as shown below (Formula I):

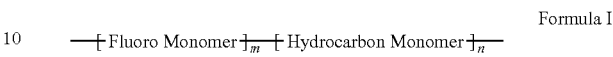

Formula I where m and n can be positive integers ranging from 1 to 100,000.

The fluoro monomers are generally fluorinated alkylene monomers and can be unsubstituted or substituted fluorinated ethylene. In one embodiment, the fluoro monomer is a substituted fluorinated ethylene bearing a substituent (R) such as —CF$_2$—CRF—, —CHF—CRF—, —CH$_2$—CRF—, —CF$_2$—CRH—, and —CFH—CRH—. R can be hydrogen, Cl, Br, I, methyl, ethyl, n-propyl, isopropyl, short chain alkyl groups, phenyl, substituted phenyl, cyclic alkyl, heterocyclic, heteroaryl, fluorinated short chain alkyl groups, fluorinated phenyl, fluorinated cyclic alkyl, fluorinated heterocyclic, or combinations thereof. Some exemplary fluorinated alkylene monomers include tetrafluoroethylene, trifluoroethylene, vinylidene fluoride, chlorotrifluoroethylene, pentafluoropropene, hexafluoropropene, vinyl fluoride, and —CHF—CHF—.

The hydrocarbon monomers can be any hydrocarbon vinyl monomers or substituted hydrocarbon vinyl monomers capable of forming biocompatible polymers. The hydrocarbon vinyl monomers generally have the formulae CHR=CH$_2$ or CR$_2$=CH$_2$ in which R can be hydrogen, methyl, ethyl, n-propyl, isopropyl, short chain alkyl groups, phenyl, substituted phenyl, cyclic alkyl, heterocyclic, heteroaryl, or combinations thereof. Representative hydrocarbon vinyl monomers include isobutylene, styrene, methyl styrene, and alkyl substituted styrene. Other hydrocarbon monomers that will yield biocompatible polymers include, but are not limited to, ethylene, propylene, and butylene.

In another embodiment, the hydrocarbon monomer can be a non vinyl monomer. Useful non vinyl monomers include CHR=CHR or CR$_2$=CHR in which R can be methyl, ethyl, n-propyl, isopropyl, short chain alkyl groups, phenyl, substituted phenyl, cyclic alkyl, heterocyclic, heteroaryl, or combinations thereof. Representative non vinyl monomers include, but are not limited to, 2-butylene, 2-pentene, 2-hexene, and 3-hexene.

In the polymer of Formula I, the fluoro monomers generally account for about 25.01 mole % to about 99.99 mole %, or more narrowly, 50.01 mole % to about 94.99% of the total monomers forming the polymer, and the hydrocarbon monomers generally account for about 0.01 mole % to about 74.99 mole % mole %, or more narrowly 5.01 mole % to about 49.99 mole % of the total monomers forming the polymer. By varying the mole percentages of the two components of the polymer, one can fine-tune physical properties of the polymer. The polymer described herein can be a random or block copolymer.

In another embodiment, it is provided a polymer blend that includes a polymer that has fluorinated monomers and at least one other biocompatible polymer. In one embodiment, the polymer that has fluorinated monomers has a structure of Formula I as defined above.

The polymer or polymer blends described herein, optionally with a bioactive agent, can be used to form an implantable device such as a stent or coating(s) on an implantable device such as a stent. Some exemplary bioactive agents are paclitaxel, docetaxel, estradiol, nitric oxide donors, super oxide dismutases, super oxide dismutases mimics, 4-amino-2,2,6,6-tetramethylpiperidine-l-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat, prevent or ameliorate a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

DETAILED DESCRIPTION

Provided herein is a polymer containing fluorinated monomers and hydrocarbon monomers. The fluorinated monomers can provide mechanical strength for the polymer. The hydrocarbon monomers impart flexibility to the polymer. The polymer or polymer blends described herein, optionally with a bioactive agent, can be used to form an implantable device such as a stent or coating(s) on an implantable device such as a stent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat, prevent or ameliorate a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

Polymers of Fluorinated Monomers and Hydrophilic Monomers

In one embodiment, the polymer can be a random or block polymer having a general formula as shown below (Formula I):

Formula I where m and n can be positive integers ranging from, e.g., 1 to 100,000.

The fluoro monomers are generally fluorinated alkylene monomers and can be unsubstituted or substituted fluorinated ethylene. In one embodiment, the fluoro monomer is a substituted fluorinated ethylene bearing a substituent (R) such as —$CF_2$—CRF—, —CHF—CRF—, —$CH_2$—CRF—, —$CF_2$—CRH—, and —CFH—CRH—. R can be hydrogen, Cl, Br, I, methyl, ethyl, n-propyl, isopropyl, short chain alkyl groups, phenyl, substituted phenyl, cyclic alkyl, heterocyclic, heteroaryl, fluorinated short chain alkyl groups, fluorinated phenyl, fluorinated cyclic alkyl, fluorinated heterocyclic, or combinations thereof. Some exemplary fluorinated alkylene monomers include tetrafluoroethylene, trifluoroethylene, vinylidene fluoride, chlorotrifluoroethylene, pentafluoropropene, hexafluoropropene, vinyl fluoride, and —CHF—CHF—.

The hydrocarbon monomers can be any hydrocarbon vinyl monomers or substituted hydrocarbon vinyl monomers capable of forming biocompatible polymers. The hydrocarbon vinyl monomers generally have the formulas CHR=$CH_2$ or $CR_2$=$CH_2$ in which R can be hydrogen, methyl, ethyl, n-propyl, isopropyl, short chain alkyl groups, phenyl, substituted phenyl, cyclic alkyl, heterocyclic, heteroaryl, or combinations thereof. Representative hydrocarbon vinyl monomers include isobutylene, styrene, methyl styrene, and alkyl substituted styrene. Other hydrocarbon monomers that will yield biocompatible polymers include, but are not limited to, ethylene, propylene, butylene.

In the polymer of Formula I, the fluoro monomers generally account for about 25.01 mole % to about 99.99 mole %, or more narrowly, 50.01 mole % to about 94.99% of the total repeating units forming the polymer, and the hydrocarbon monomers generally account for about 0.01 mole % to about 74.99 mole % mole %, or more narrowly 5.01 mole % to about 49.99 mole % of the total repeating units forming the polymer. By varying the mole percentages of the two components of the polymer, one can fine-tune physical properties of the polymer. The polymer described herein can be a random or block copolymer.

In one embodiment, the polymer of formula I has a structure of formula II or formula III:

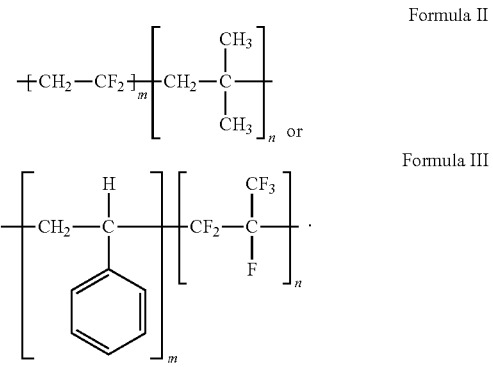

The polymer described herein can be synthesized by methods known in the art (see, for example, D. Braun, et al., Polymer Synthesis: Theory and Practice. Fundamentals, Methods, Experiments. $3^{rd}$ Ed., Springer, 2001; Hans R. Kricheldorf, Handbook of Polymer Synthesis, Marcel Dekker Inc., 1992). For example, one method that can be used to make the polymer can be free radical methods (see, for example, D. Braun, et al., Polymer Synthesis: Theory and Practice. Fundamentals, Methods, Experiments. $3^{rd}$ Ed., Springer, 2001; Hans R. Kricheldorf, Handbook of Polymer Synthesis, Marcel Dekker Inc., 1992). Polymerization in solvent can also be used to synthesize the polymer described herein.

Copolymerization prevents phase separation on a large scale. For systems where the reactivity ratios greatly differ, a random polymerization will result in more and more of a block structure. Otherwise, polymerizations that proceed step-wise via the formation of prepolymers may be used to achieve block structures (See, for example, J. Kopecek, et al., Prog. Polym. Sci, 9:34 (1983).

Polymer Blends

In another embodiment, the polymer of formulae I-III can be blended with another biocompatible polymer to form a coating material for an implantable device. The biocompatible polymer can be biodegradable or nondegradable. Representative examples of these biocompatible polymers include, but are not limited to, poly(ester amide), polyesters, polyhydroxyalkanoates (PHA), poly(3-hydroxyalkanoates) such as poly(3-hydroxypropanoate), poly(3-hydroxybutyrate), poly (3-hydroxyvalerate), poly(3-hydroxyhexanoate), poly(3-hydroxyheptanoate) and poly(3-hydroxyoctanoate), poly(4-hydroxyalknaotes) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly (ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyolefins, polyisobutylene and ethylene-alphaolefin copolymers, poly(methylmethacrylate), poly(ethyl methacrylate), poly(isopropyl methacrylate), poly(n-propyl methacrylate), poly(n-butyl methacrylate), methacrylic polymers and copolymers, acrylic polymers and copolymers, vinyl halide polymers and copolymers, such as polyvinyl chloride, poly(vinylidene fluoride), poly(vinylidene fluoride-co-hexafluoropropylene), polyvinyl ethers such as polyvinyl methyl ether, polyvinylidene halides such as polyvinylidene chloride, polyacrylonitrile, polyvinyl ketones, polyvinyl aromatics such as polystyrene, polyvinyl esters such as polyvinyl acetate, copolymers of vinyl monomers with each other and olefins such as ethylene-methyl methacrylate copolymers, acrylonitrile-styrene copolymers, ABS resins, and ethylene-vinyl acetate copolymers, polyamides such as Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters), e.g., copoly(ethylene oxide-co-lactic acid) (PEO/PLA), polyalkylene oxides such as poly(ethylene oxide) and poly(propylene oxide), polyalkylene oxalates, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly (methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, and combinations thereof. In some embodiments, the polymer can exclude any one of the aforementioned polymers.

As used herein, the terms poly(D,L-lactide) (PDLL), poly (L-lactide) (PLL), poly(D,L-lactide-co-glycolide) (PDLLG), and poly(L-lactide-co-glycolide) (PLLG) are used interchangeably with the terms poly(D,L-lactic acid) (PDLLA), poly(L-lactic acid) (PLLA), poly(D,L-lactic acid-co-glycolic acid) (PDLLAGA), and poly(L-lactic acid-co-glycolic acid) (PLLAGA), respectively.

Bioactive Agents

In accordance with a further embodiment of the invention, the polymer or polymer blend described herein can form a coating that may optionally include one or more active agents. The bioactive agent can be any agent that is biologically active, for example, a therapeutic, prophylactic, or diagnostic agent.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator, antigens for immunization, hormones and growth factors, polysaccharides such as heparin, oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

In the case of controlled release, a wide range of different bioactive agents can be incorporated into a controlled release device. These include hydrophobic, hydrophilic, and high molecular weight macromolecules such as proteins. The bioactive compound can be incorporated into polymeric coating in a percent loading of between 0.01% and 70% by weight, more preferably between 5% and 50% by weight.

In one embodiment, the bioactive agent can be for inhibiting the activity of vascular smooth muscle cells. More specifically, the bioactive agent can be aimed at inhibiting abnormal or inappropriate migration and/or proliferation of smooth muscle cells for the inhibition of restenosis. The bioactive agent can also include any substance capable of exerting a therapeutic or prophylactic effect in the practice of the present invention. For example, the bioactive agent can be for enhancing wound healing in a vascular site or improving the structural and elastic properties of the vascular site. Examples of active agents include antiproliferative substances such as actinomycin D, or derivatives and analogs thereof (manufactured by Sigma-Aldrich 1001 West Saint Paul Avenue, Milwaukee, Wis. 53233, or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include alpha-interferon, genetically engineered epithelial cells, anti-inflammatory agents, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, cytostatic agents, prodrugs thereof, co-drugs thereof, or a combination thereof.

The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, closure devices for patent foramen ovale, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP2ON," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate, and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, atherosclerosis, thrombosis, and restenosis. Stents may be placed in a wide array of blood vessels, both arteries and veins. Representative examples of sites include the iliac, renal, carotid, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter, which allows a stent in its collapsed configuration to be inserted into the passageway. The delivery catheter is inserted either percutaneously, or by surgery, into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth prophetic examples. All parameters and data are not to be construed to unduly limit the scope of the embodiments of the invention.

Example 1

Synthesis of Poly(Block-Vinylidene Fluoride-Co-Block-Isobutylene)

Fluoropolymers are typically synthesized by free radical polymerization, using suspension or emulsion techniques, while polyisobutylene is typically produced via cationic polymerization methods (see G. Odian, Principles of Polymerization, $3^{rd}$ Ed., John Wiley & Sons, N.Y., 1991). However, fluoropolymers can also be synthesized by atom transfer radical polymerization (ATRP) using iodine or bromine functional initiators. These polymerizations result in PVDF with terminal iodine or bromine groups. These endgroups can then be used directly, or functionalized, to serve as carbocationic initiators for isobutylene. A block co-polymer can be made by first synthesizing a bromo-terminated poly(vinylidene fluoride) via ATRP techniques (see Z. Zhang, et al. "Synthesis of fluorine-containing block copolymers via ATRP 1. Synthesis and characterization of PSt-PVDF-PSt triblock copolymers", Polymer (40) (1999) 1341-1345). The resulting bromo-terminated PVDF can then be used as an initiator in a cationic polymerization catalyzed by a lewis acid such as titanium tetrachloride, titanium tetrabromide, or aluminum trichloride (see J. P. Kennedy, et al. "Design Polymers by carbocationic Macromolecular Engineering", Hanser, N.Y., Munich, 1992). A useful weight ratio of vinylidene fluoride to isobutylene is 75/25.

Example 2

Synthesis of Poly(Vinylidene Fluoride-Co-Styrene)

Both monomers are amenable to free radical polymerization. This polymerization can be via suspension or emulsion polymerization techniques. Useful initiators are peroxides, organic soluble peroxides, persulfate compounds, and azo compounds. Redox systems such as compounds containing ferrous, sulfite, or bisulfite ions can be used to produce desirable initiation rates at low temperatures. One useful route is suspension polymerization in an autoclave. A vinylidene fluoride/styrene copolymer dispersion can be prepared having a composition of 90% vinylidene fluoride and 10% styrene by weight. To a 10 gallon glass-lined autoclave is added 5 gallons of deionized water, and charged with 2.2 kg of vinylidene fluoride (VDF) and 0.24 kg of styrene. After sparging with nitrogen to remove all oxygen, and with rapid stirring, a solution of 20 gm of a 70% solution of tertiary butyl hydroperoxide (TBHP) that is diluted to 100 ml with deionized water is added. Next, a solution of 15 gm of sodium metabisulfite (MBS), and 2.2 gm of ferrous sulfate heptahydrate, dissolved in 100 ml of deionized water is added. The autoclave is maintained at 15-20° C. After addition if the initial catalysts, 300 ml of perfluorinated ammonium octoanate catalyst (20% active solids) is charged into the autoclave. The polymerization is continued by slow addition of two separate solutions consisting of 100 gm of TBHP diluted to 700 ml with deionized water and 80 gm of MBS diluted to 750 ml with deionized water. These initiators are added at a rate of 1.8 ml/min. After consumption if the initial charge of VDF and styrene, 18 kg of VDF and 2 kg of styrene are added over a period of 5 hours. The autoclave is vented, yielding a polymer dispersion in water which is isolated by sieving and rinsed.

Example 3

Coating a Stent with the Composition of Example 2

A composition can be prepared by mixing the following components:

(a) about 2.0% (w/w) of poly(butyl methacrylate) (PBMA), and (b) the balance a 50/50 (w/w) blend of acetone and cyclohexanone. The composition can be applied onto the surface of bare 12 mm small VISION™ stent (Guidant Corp.). The coating can be sprayed and dried to form a primer layer. A spray coater can be used having a 0.014 round nozzle maintained at ambient temperature with a feed pressure 2.5 psi (0.17 atm) and an atomization pressure of about 15 psi (1.02 atm). About 20 µg of the coating can be applied at per one spray pass. About 80 µg of wet coating can be applied, and the stent can be dried for about 10 seconds in a flowing air stream at about 50° C. between the spray passes. The stents can be baked at about 80° C. for about one hour, yielding a drug reservoir layer composed of approximately 60 µg of PBMA.

A second composition can be prepared by mixing the following components:

(a) about 2.0% (w/w) of the polymer of example 2;

(b) about 1.0% (w/w) of everolimus, (c) the balance a 50/50 (w/w) blend of acetone and dimethylformamide.

The second composition can be applied onto the dried primer layer to form a drug reservoir layer using the same spraying technique and equipment used for applying the reservoir. About 200 µg of wet coating can be applied followed by drying and baking at about 50° C. for about 2 hours, yielding a dry drug reservoir layer having solids content of about 180 µg and containing about 60 µg of everolimus.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable device comprising a polymer blend comprising a first biocompatible polymer and at least one other biocompatible polymer, wherein the first biocompatible polymer comprises fluorinated monomers and hydrocarbon monomers,
   wherein the hydrocarbon monomers are CHR=CH$_2$ or CR$_2$=CH$_2$ in which R is selected from the group consisting of methyl, ethyl, n-propyl, isopropyl, short chain alkyl groups, phenyl, substituted phenyl, cyclic alkyl, heterocyclic alkyl, and heteroaryl,
   wherein the fluorinated monomers are selected from the group consisting of —CH$_2$—CHF—, —CHF—CHF—, —CClF—CF$_2$—, —CF$_2$—C(CF$_3$)F—, —CHF—C(CF$_3$)F—, —CF$_2$—C(CF$_3$)H—, —CF$_2$—CR'F—, —CHF—CR'F—, —CF$_2$—CR'H—, —CH$_2$—CR'F—, and —CFH—CR'H— where R' is independently selected from the group consisting of Cl, Br, I, methyl, ethyl, n-propyl, iosopropyl, short chain alkyl groups, phenyl, substituted phenyl, cyclic alkyl, heterocyclic, heteroaryl, fluorinated short chain alkyl groups, fluorinated phenyl, fluorinated cyclic alkyl, fluorinated heterocyclic, and combinations thereof,
   wherein the fluorinated monomers form about 25.01 mole % to about 99.99 mole % repeating units of the polymer, and
   wherein the hydrocarbon monomers form about 74.99 mole % to about 0.01 mole % repeating units of the polymer.

2. The implantable device of claim 1, wherein the fluorinated monomers form about 50.01 mole % to about 94.99 mole % units of the polymer, and
   wherein the hydrocarbon monomers form about 49.99 mole % to about 5.01 mole % repeating units of the polymer.

3. The implantable device of claim 1, wherein the other biocompatible polymer is selected from the group consisting of poly(ester amide), polyesters, polyhydroxyalkanoates (PHA), poly(3-hydroxyalkanoates), poly(3-hydroxypropanoate), poly(3-hydroxybutyrate), poly(3-hydroxyvalerate), poly(3-hydroxyhexanoate), poly(3-hydroxyheptanoate), poly(3-hydroxyoctanoate), poly(4-hydroxyalknaotes), poly(4-hydroxybutyrate), poly(4-hydroxyvalerate), poly(4-hydroxyhexanote), poly(4-hydroxyheptanoate), poly(4-hydroxyoctanoate) copolymers including 3-hydroxyalkanoate, 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyolefins, polyisobutylene and ethylene-alphaolefin copolymers, methacrylic polymers and copolymers, acrylic polymers and copolymers, poly(methylmethacrylate), poly(ethyl methacrylate), poly(isopropyl methacrylate), poly(n-propyl methacrylate), poly(n-butyl methacrylate), vinyl halide polymers and copolymers polyvinyl chloride, polyvinyl ethers polyvinyl methyl ether, polyvinylidene halides, polyvinylidene chloride, polyacrylonitrile, polyvinyl ketones, polyvinyl aromatics, polystyrene, polyvinyl esters, polyvinyl acetate, copolymers of vinyl monomers, ethylene-methyl methacrylate copolymers, acrylonitrile-styrene copolymers, ABS resins, and ethylene-vinyl acetate copolymers, polyamides, Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers, poly(ethylene glycol) (PEG), copoly(ether esters), copoly(ethylene oxide-co-lactic acid) (PEO/PLA), polyalkylene oxides, poly(ethylene oxide), poly(propylene oxide), polyalkylene oxalates, phosphoryl choline, choline, poly(aspirin), polymers and copolymers of hydroxyl bearing monomers, polymers and copolymers of hydroxyethyl methacrylate (HEMA), polymers and copolymers of hydroxypropyl methacrylate (HPMA), polymers and copolymers of hydroxypropylmethacrylamide, polymers and copolymers of PEG acrylate (PEGA), polymers and copolymers of PEG methacrylate, polymers and copolymers of 2-methacryloyloxyethylphosphorylcholine (MPC), polymers and copolymers of n-vinyl pyrrolidone (VP), polymers and copolymers of carboxylic acid bearing monomers, polymers and copolymers of methacrylic acid (MA), polymers and copolymers of acrylic acid (AA), polymers and copolymers of alkoxymethacrylate, polymers and copolymers of alkoxyacrylate, polymers and copolymers of 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), polypropylene oxide-co-polyethylene glycol, poly(tetramethylene glycol), hydroxy functional poly(vinyl pyrrolidone), biomolecules, collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, and combinations thereof.

4. The implantable device of claim 1, wherein the hydrocarbon monomer is selected from the group consisting of one or more isobutylene, styrene, methyl styrene, and alkyl substituted styrene.

5. The implantable device of claim 1, wherein the first biocompatible polymer has a structure of formula III:

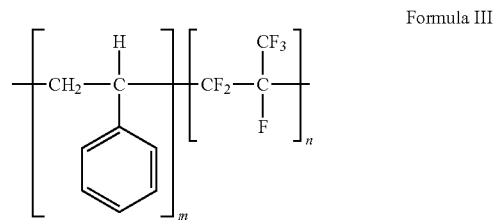

Formula III wherein m and n are positive integers ranging from 1 to 100,000.

6. The implantable device of claim 1, which is a stent.

7. The implantable device of claim 6, further comprising a bioactive agent.

8. The implantable device of claim 7, wherein the bioactive agent is selected from the group consisting of paclitaxel, docetaxel, estradiol, nitric oxide donors, super oxide dismutases, super oxide dismutases mimics, 4-amino -2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and a combination thereof.

9. The implantable device of claim 6, wherein the polymer blend is included in a coating on the stent.

10. The implantable device of claim 7, wherein the polymer blend and the bioactive agent are included in a coating on the stent.

11. The implantable device of claim 8, wherein the polymer blend and the bioactive agent are included in a coating on the stent.

12. The implantable device of claim 6, wherein the polymer blend is included in the body structure of the stent.

13. The implantable device of claim 7, wherein the polymer blend and the bioactive agent are included in the body structure of the stent.

14. The implantable device of claim 8, wherein the polymer blend and the bioactive agent are included in the body structure of the stent.

\* \* \* \* \*